United States Patent
Neyts et al.

(10) Patent No.: US 8,796,273 B2
(45) Date of Patent: Aug. 5, 2014

(54) COMPOUND FOR THE TREATMENT OF ENTEROVIRUSES

(75) Inventors: Johan Neyts, Leuven (BE); Armando De Palma, Leuven (BE); Hendrik Jan Thibaut, Leuven (BE); Pieter Leyssen, Leuven (BE); Simon Tucker, Notting Hill (AU)

(73) Assignee: Biota Scientific Management Pty Ltd, Notting Hill (AU)

( * ) Notice: Subject to any disclaimer, the term of this patent is extended or adjusted under 35 U.S.C. 154(b) by 266 days.

(21) Appl. No.: 13/168,263

(22) Filed: Jun. 24, 2011

(65) Prior Publication Data

US 2012/0022073 A1  Jan. 26, 2012

(30) Foreign Application Priority Data

Jun. 25, 2010 (AU) ................................ 2010902823

(51) Int. Cl.
| | |
|---|---|
| A61K 31/501 | (2006.01) |
| A61K 31/42 | (2006.01) |
| A61K 31/415 | (2006.01) |
| A61K 31/422 | (2006.01) |
| A61K 31/4184 | (2006.01) |

(52) U.S. Cl.
CPC ........... *A61K 31/501* (2013.01); *A61K 2300/00* (2013.01); *A61K 31/422* (2013.01); *A61K 31/4184* (2013.01)
USPC ........................ 514/252.03; 514/378; 514/395

(58) Field of Classification Search
USPC ....................... 514/252.03, 378, 395
See application file for complete search history.

(56) References Cited

U.S. PATENT DOCUMENTS

2004/0077633 A1 * 4/2004 Watson et al. ................ 514/218

FOREIGN PATENT DOCUMENTS

| WO | WO 02/50045 A1 | 6/2002 |
| WO | WO 2009/143571 A1 | 12/2009 |

OTHER PUBLICATIONS

De Palma et al. "Selective inhibitors of picornavirus replication," Medicinal Research Reviews, 2008, Wiley Periodicals Inc. Published online in Wiley InterScience (www.Interscience.wiley.com) DOI 10.1002/med 20125.*

Thibaut et al., "Towards the design of combination therapy for the treatment of enterovirus infections," *Antiviral Research* 90: 213-217, 2011.

* cited by examiner

*Primary Examiner* — Shengjun Wang
(74) *Attorney, Agent, or Firm* — B. Aaron Schulman, Esq; Stites & Harbison, PLLC.

(57) ABSTRACT

The present invention relates to the treatment, alleviation, prevention or reduction in the incidence of symptoms, diseases or conditions resulting from or associated with enteroviruses, more particularly the enteroviral infections they cause.

7 Claims, 2 Drawing Sheets

A

B

C

D

COMPOUND FOR THE TREATMENT OF ENTEROVIRUSES

BACKGROUND

1. Technical Field

The present invention relates to the treatment, alleviation, prevention or reduction in the incidence of symptoms, diseases or conditions resulting from or associated with enteroviruses, more particularly the enteroviral infections they cause.

2. Description of the Related Art

The Picornaviridae family of viruses, containing the genus *Enterovirus*, are nonenveloped viruses with a single-stranded RNA genome of positive polarity.

Serotypes of the genus *Enterovirus* were originally classified into three groups, namely the polioviruses, group A and B coxsackieviruses and echoviruses. Since 1969 new enterovirus serotypes, that might otherwise have fallen within these three groups, have been named numerically with an enterovirus (EV) number starting from 68 (i.e. EV68) (see for example Knipe, D M, Howley P M et. al. eds *Fields Virology* 5$^{th}$ ed. Volume 1 Section II Philadelphia, Pa.: Lippincott Williams & Wilkins (2007)). Under a new classification scheme from the International Committee on Taxonomy of Viruses (ICTV) the following ten species are now included in the genus *Enterovirus*: Human enterovirus A (HEV-A), Human enterovirus B (HEV-B), Human enterovirus C (HEV-C), Human enterovirus D (HEV-D), Bovine enterovirus, Porcine enterovirus B, Simian enterovirus A, Human rhinovirus A, Human rhinovirus B and Human rhinovirus C (see for example ICTV Master Species List 2009 Version 4). The four species HEV-A, HEV-B, HEV-C and HEV-D include the polioviruses, group A and B coxsackieviruses, echoviruses and enterovirus serotypes EV68 onwards. Within the species HEV-A, HEV-B, HEV-C and HEV-D the enterovirus serotypes may accordingly be categorised as non-polio enterovirus serotypes (an expression used herein to embrace group A and B coxsackieviruses, echoviruses and enterovirus serotypes from EV68 onwards) and poliovirus serotypes.

Prior to 2008 the rhinoviruses did not fall within the genus *Enterovirus* and were given their own genus *Rhinovirus*, of the Picornaviridae family. Rhinoviruses are acid-labile viruses which replicate in the nasopharynx and may also replicate in the lower respiratory tract whereas the members of the species HEV-A, HEV-B, HEV-C and HEV-D replicate in the alimentary tract and accordingly retain infectivity at pH values of 3.0 and sometimes lower.

Following replication in the alimentary tract, members of the species HEV-A, HEV-B, HEV-C and HEV-D typically enter the bloodstream where they may affect a variety of tissues and organs thereby causing a diversity of conditions or diseases. Potential targets include the skin and central nervous system (CNS). Transmission of the virus is usually by the faeco-oral or respiratory route and is increased by poor hygiene and overcrowded living conditions.

Members of the species HEV-A, HEV-B, HEV-C and HEV-D, are responsible for a wide range of viral infections which cause or are associated with a wide variety of symptoms, diseases or conditions such as viral meningitis, encephalitis, gastroenteritis, pancreatitis, fever, paralysis, myocarditis/pericarditis, pneumonia, bronchiolitis, croup, sepsis and hand foot and mouth disease and have even been suspected of having a role in the onset of type 1 diabetes. In some instances enteroviral infections may result in severe, life-threatening complications and even death. Children, especially those under the age of five, are the most susceptible to enteroviral infections.

The poliovirus subgenus classification comprises three serotypes of polioviruses, numbered PV1, PV2 and PV3. Children under the age of five are at most risk of the highly infectious disease which may lead to irreversible paralysis usually of the legs and in some cases death due to immobilisation of breathing muscles. There is no known cure for polio although two forms of polio vaccine, namely the Salk inactivated polio vaccine (IPV) and the Sabin live attenuated vaccine (OPV, oral polio vaccine), may be administered as a preventative measure. In recent times a global effort to eradicate the disease by polio vaccination in early childhood has seen the incidence of polio cases decrease (down by approximately 99% in the period 1988 to 2008). By 2008 only Afghanistan, India, Nigeria and Pakistan remain polio-endemic. Unfortunately, children in all countries still remain at risk of contracting the disease as long as any child has the infection. This risk was most recently highlighted when a number of polio-free countries were re-infected with imports of the disease in 2003 to 2005 and in 2008 to 2009.

The non-polio enteroviruses within the species HEV-A, HEV-B, HEV-C and HEV-D comprise the subgenera coxsackieviruses A (such as serotypes 1-22 and 24), coxsackieviruses B (such as serotypes 1-6), echoviruses (such as serotypes 1-7, 9, 11-27, 29-34) and the more recently classified enteroviruses (such as serotypes EV68 onwards). In the US alone it is estimated that non-polio enteroviruses within the species HEV-A, HEV-B, HEV-C and HEV-D are responsible for approximately 10-20 million cases of symptomatic infections annually. The incidence of infections is generally influenced by seasons and climates. Generally, countries which experience temperate climates are likely to observe higher incidences of infections in the summer and autumn months whereas countries with subtropical and tropical climates are likely to experience infections year-round. An increasing number of pandemics caused by EV71 infections have been reported in recent times which are of particular concern given their association with fatalities. The EV71 virus' propensity to cause severe neurological conditions or diseases is also of particular concern. Non-polio enteroviral infections, such as EV71 infections, are therefore an ever increasing public health concern given the risk of life-threatening complications associated with the symptoms, diseases and conditions they cause and the lack of an approved effective therapy for their prevention or treatment.

There are no approved antiviral agents or vaccines for the treatment or prevention of infections caused by serotypes of one or more of the species HEV-A, HEV-B, HEV-C and HEV-D, with the exception of the two prophylactic forms of polio vaccine. Accordingly, there remains an ongoing need for an antiviral agent effective against serotypes of one or more of the species HEV-A, HEV-B, HEV-C and HEV-D, the enteroviral infections they cause and the symptoms, conditions or diseases arising from them.

SUMMARY

It has now been discovered that a particular compound, namely 3-ethoxy-6-{2-[1-(6-methyl-pyridazin-3-yl)-piperidin-4-yl]-ethoxy}-benzo[d]isoxazole, is a potent anti-enteroviral agent and is therefore useful in the treatment, alleviation, prevention or reduction of symptoms, diseases or conditions associated with serotypes of one or more of the species Human enterovirus A, Human enterovirus B, Human enterovirus C and Human enterovirus D, including polioviruses and non-polioenteroviruses, which include coxsackieviruses A (such as serotypes 1-22 and 24), coxsackieviruses B (such as serotypes 1-6), echoviruses (such as serotypes 1-7, 9, 11-27, 29-34) and enteroviruses (such as serotypes EV68-71).

According to one aspect there is provided a method for treating or alleviating an enteroviral infection caused by a serotype of one or more of the species Human enterovirus A, Human enterovirus B, Human enterovirus C and Human enterovirus D comprising administering 3-ethoxy-6-{2-[1-(6-methyl-pyridazin-3-yl)-piperidin-4-yl]-ethoxy}-benzo[d]isoxazole or a pharmaceutically acceptable salt thereof to a subject suffering from said infection.

In another aspect there is provided the use of 3-ethoxy-6-{2-[1-(6-methyl-pyridazin-3-yl)-piperidin-4-yl]-ethoxy}-benzo[d]isoxazole or a pharmaceutically acceptable salt thereof in the manufacture of a medicament for the treatment or alleviation of an enteroviral infection caused by a serotype of one or more of the species Human enterovirus A, Human enterovirus B, Human enterovirus C and Human enterovirus D.

In another aspect there is provided 3-ethoxy-6-{2-[1-(6-methyl-pyridazin-3-yl)-piperidin-4-yl]-ethoxy}-benzo[d]isoxazole or a pharmaceutically acceptable salt thereof for use in the treatment or alleviation of an enteroviral infection caused by a serotype of one or more of the species Human enterovirus A, Human enterovirus B, Human enterovirus C and Human enterovirus D.

In another aspect there is provided a method for preventing or reducing the incidence of an enteroviral infection caused by a serotype of one or more of the species Human enterovirus A, Human enterovirus B, Human enterovirus C and Human enterovirus D comprising administering 3-ethoxy-6-{2-[1-(6-methyl-pyridazin-3-yl)-piperidin-4-yl]-ethoxy}-benzo[d]isoxazole or a pharmaceutically acceptable salt thereof to a subject at risk of said infection.

In another aspect there is provided the use of 3-ethoxy-6-{2-[1-(6-methyl-pyridazin-3-yl)-piperidin-4-yl]-ethoxy}-benzo[d]isoxazole or a pharmaceutically acceptable salt thereof in the manufacture of a medicament for the prevention or reduction of the incidence of an enteroviral infection caused by a serotype of one or more of the species Human enterovirus A, Human enterovirus B, Human enterovirus C and Human enterovirus D.

In another aspect there is provided 3-ethoxy-6-{2-[1-(6-methyl-pyridazin-3-yl)-piperidin-4-yl]-ethoxy}-benzo[d]isoxazole or a pharmaceutically acceptable salt thereof for use in preventing or reducing the incidence of an enteroviral infection caused by a serotype of one or more of the species Human enterovirus A, Human enterovirus B, Human enterovirus C and Human enterovirus D.

In yet another aspect there is provided a method for treating or alleviating symptoms, diseases or conditions resulting from or associated with an enteroviral infection caused by a serotype of one or more of the species Human enterovirus A, Human enterovirus B, Human enterovirus C and Human enterovirus D comprising administering 3-ethoxy-6-{2-[1-(6-methyl-pyridazin-3-yl)-piperidin-4-yl]-ethoxy}-benzo[d]isoxazole or a pharmaceutically acceptable salt thereof to a subject suffering from said disease or condition or symptoms thereof.

In another aspect there is provided the use of 3-ethoxy-6-{2-[1-(6-methyl-pyridazin-3-yl)-piperidin-4-yl]-ethoxy}-benzo[d]isoxazole or a pharmaceutically acceptable salt thereof in the manufacture of a medicament for the treatment or alleviation of symptoms, diseases or conditions resulting from or associated with an enteroviral infection caused by a serotype of one or more of the species Human enterovirus A, Human enterovirus B, Human enterovirus C and Human enterovirus D.

In another aspect there is provided 3-ethoxy-6-{2-[1-(6-methyl-pyridazin-3-yl)-piperidin-4-yl]-ethoxy}-benzo[d]isoxazole or a pharmaceutically acceptable salt thereof for use in the treatment or alleviation of symptoms, diseases or conditions resulting from or associated with an enteroviral infection caused by a serotype of one or more of the species Human enterovirus A, Human enterovirus B, Human enterovirus C and Human enterovirus D.

In still another aspect there is provided a method for preventing or reducing the incidence of symptoms, diseases or conditions resulting from or associated with an enteroviral infection caused by a serotype of one or more of the species Human enterovirus A, Human enterovirus B, Human enterovirus C and Human enterovirus D comprising administering 3-ethoxy-6-{2-[1-(6-methyl-pyridazin-3-yl)-piperidin-4-yl]-ethoxy}-benzo[d]isoxazole or a pharmaceutically acceptable salt thereof to a subject suffering from said disease or condition or symptoms thereof.

In another aspect there is provided the use of 3-ethoxy-6-{2-[1-(6-methyl-pyridazin-3-yl)-piperidin-4-yl]-ethoxy}-benzo[d]isoxazole or a pharmaceutically acceptable salt thereof in the manufacture of a medicament for the prevention or reduction of the incidence of symptoms, diseases or conditions resulting from or associated with an enteroviral infection caused by a serotype of one or more of the species Human enterovirus A, Human enterovirus B, Human enterovirus C and Human enterovirus D.

In another aspect there is provided 3-ethoxy-6-{2-[1-(6-methyl-pyridazin-3-yl)-piperidin-4-yl]-ethoxy}-benzo[d]isoxazole or a pharmaceutically acceptable salt thereof for use in the prevention or reduction of the incidence of symptoms, diseases or conditions resulting from or associated with an enteroviral infection caused by a serotype of one or more of the species Human enterovirus A, Human enterovirus B, Human enterovirus C and Human enterovirus D.

In another aspect there is provided combined use of 3-ethoxy-6-{2-[1-(6-methyl-pyridazin-3-yl)-piperidin-4-yl]-ethoxy}-benzo[d]isoxazole or a pharmaceutically acceptable salt thereof with a second anti-enteroviral agent for the treatment, alleviation, prevention or reduction in the incidence of symptoms, diseases or conditions resulting from or associated with an enteroviral infection caused by a serotype of one or more of the species Human enterovirus A, Human enterovirus B, Human enterovirus C and Human enterovirus D. For example, a method of the invention may further comprise the step of administering a second anti-enteroviral agent either simultaneously (separately or as a composition) or sequentially. By way of further example, a medicament prepared according to the invention may further comprise a second anti-enteroviral agent.

In some embodiments a method of the invention may further comprise a step of diagnosis, whereby a subject is selected on the basis of requiring treatment, alleviation, prevention or reduction of symptoms, diseases or conditions associated with an enteroviral infection caused by a serotype of one or more of the species Human enterovirus A, Human enterovirus B, Human enterovirus C and Human enterovirus D. In some embodiments a medicament prepared according to the invention may be intended for use by a subject selected on the basis of requiring treatment, alleviation, prevention or reduction of symptoms, diseases or conditions associated with an enteroviral infection caused by a serotype of one or more of the species Human enterovirus A, Human enterovirus B, Human enterovirus C and Human enterovirus D.

In some embodiments the serotype of one or more of the species Human enterovirus A, Human enterovirus B, Human enterovirus C and Human enterovirus D is a poliovirus. In some embodiments the serotype of one or more of the species Human enterovirus A, Human enterovirus B, Human enterovirus C and Human enterovirus D is a non-polio enterovirus. In an embodiment the non-polio enterovirus is selected from enteroviruses, coxsackieviruses A and echoviruses.

In some embodiments the serotype of one or more of the species Human enterovirus A, Human enterovirus B, Human enterovirus C and Human enterovirus D is poliovirus 1 (PV1), poliovirus 2 (PV2) or poliovirus 3 (PV3). In some embodiments the serotype of one or more of the species Human enterovirus A, Human enterovirus B, Human enterovirus C and Human enterovirus D is poliovirus 1 (PV1). In some embodiments the serotype of one or more of the species Human enterovirus A, Human enterovirus B, Human enterovirus C and Human enterovirus D is coxsackievirus A9 (CVA9), coxsackievirus A16 (CVA16) or coxsackievirus A21 (CVA21). In some embodiments the serotype of one or more of the species Human enterovirus A, Human enterovirus B, Human enterovirus C and Human enterovirus D is echovirus 4 (E4), echovirus 9 (E9), echovirus 11 (E11) or echovirus 30 (E30). In some embodiments the serotype of one or more of the species Human enterovirus A, Human enterovirus B, Human enterovirus C and Human enterovirus D is enterovirus 71 (EV71).

In view of the large number of serotypes of Human enterovirus A, B, C and D, the existence of particular clinical isolates and various methods, it is expected that there will be some variation in the activity of 3-ethoxy-6-{2-[1-(6-methyl-pyridazin-3-yl)-piperidin-4-yl]-ethoxy}-benzo[d]isoxazole against the various serotypes. However, it has been shown by the present invention that the compound is effective against a wide range of serotypes which are representative of the HEV species, particularly HEV-A, HEV-B and HEV-C.

DETAILED DESCRIPTION

Figure 1:
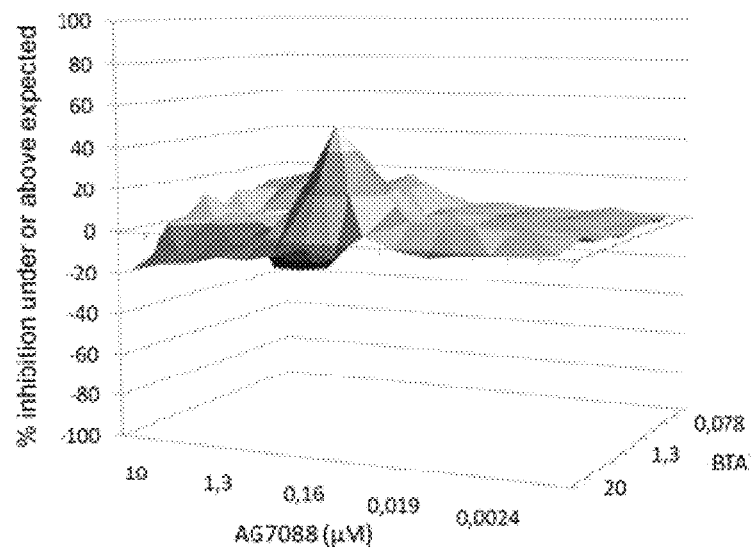
FIG. 1: Shows the combined antiviral activity of 3-ethoxy-6-{2-[1-(6-methyl-pyridazin-3-yl)-piperidin-4-yl]-ethoxy}-benzo[d]isoxazole (BTA; concentration in µM) with Rupintrivir i.e. AG-7088 (Representation A) and enviroxime (Representation B) respectively as against poliovirus Sabin 1 (PV1).
Figure 1:
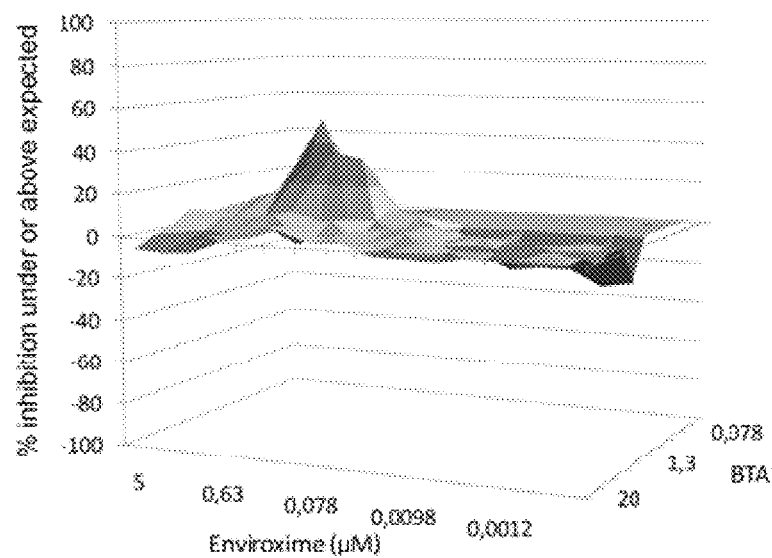

3-Ethoxy-6-{2-[1-(6-methyl-pyridazin-3-yl)-piperidin-4-yl]-ethoxy}-benzo[d]isoxazole

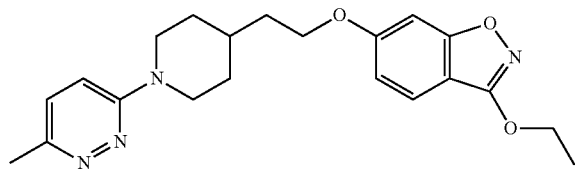 [SMILES: CCOc1noc2cc(OCCC3CCN(c4ccc(C)nn4)CC3)ccc12]

is disclosed in WO02/50045 together with results of the inhibition of the human rhinoviruses HRV-2 (serotype of human rhinovirus A) and HRV-14 (serotype of human rhinovirus B).

The present invention is predicated, in part, on the discovery that 3-ethoxy-6-{2-[1-(6-methyl-pyridazin-3-yl)-piperidin-4-yl]-ethoxy}-benzo[d]isoxazole displays both potent and broad spectrum activity against serotypes of the human enterovirus species HEV-A, HEV-B, HEV-C and HEV-D. As herein described, poliovirus serotypes and non-polio enterovirus serotypes have recently been defined taxonomically to fall within the species HEV-A, HEV-B, HEV-C and HEV-D. The serotypes of the species HEV-A, HEV-B, HEV-C and HEV-D can be distinguished from serotypes of the human rhinovirus species HRV-A, HRV-B and HRV-C based on their site of replication and/or their physical, chemical and/or biological sensitivity to external stimuli.

For example, it is known that Human rhinovirus serotypes are sensitive to acidification, whereas other serotypes of the genus *Enterovirus* are not. In particular, temporarily acidifying a solution containing a rhinovirus typically to pH 3 before neutralization reduces the infectivity of the rhinovirus significantly compared with a sample that has been maintained at pH 7. On the other hand serotypes of the species HEV-A, HEV-B, HEV-C and HEV-D are substantially insensitive to a similar treatment.

There may be a number of tests available that can demonstrate this sensitivity (see for example Lennett, E H et. al. eds. *Diagnostic Procedures for Viral, Rickettsial and Clamydial Infections* 7th ed, American Public Health Association (1995)). One such test involves adding 0.2 mL of tissue culture to 1.8 mL of HEPES buffer (comprising 4-(2-hydroxyethyl)-1-piperazineethanesulfonic acid) at pH 3 in a first tube, and another 0.2 mL of tissue culture to a second tube at pH 7, and holding both tubes at 4° C. for 1 hour. Following neutralization of the acidified culture in the first tube with 10N NaOH, the cultures in each tube are titrated for infectivity. If the unknown isolate is a rhinovirus the infectivity titer should be reduced by at least 100-fold for the acidified culture.

Accordingly 3-ethoxy-6-{2-[1-(6-methyl-pyridazin-3-yl)-piperidin-4-yl]-ethoxy}-benzo[d]isoxazole is useful in the treatment, alleviation, prevention or reduction of symptoms, diseases or conditions associated with infection caused by a virus of the genus *Enterovirus*, wherein the virus is substantially insensitive to weak acid at pH 3.

3-ethoxy-6-{2-[1-(6-methyl-pyridazin-3-yl)-piperidin-4-yl]-ethoxy}-benzo[d]isoxazole is a capsid binder. Capsid binders act by preventing uncoating and/or attachment of the virus to the host cell by binding into a hydrophobic pocket underneath the floor of a canyon on the viral capsid. Other known capsid binders include Pirodavir, Pleconaril and V-073.

Table 1 shows the surprising effect of 3-ethoxy-6-{2-[1-(6-methyl-pyridazin-3-yl)-piperidin-4-yl]-ethoxy}-benzo[d]isoxazole when compared to other capsid binders, Pirodavir, Pleconaril and V-073, on the replication of PV1 and EV71, as tested by the method of Example 1.

TABLE 1

Effect of "capsid binders" on the replication of two enteroviruses.

| Compound | Poliovirus 1 (PV1) | Enterovirus 71 (EV71) |
|---|---|---|
| 3-ethoxy-6-{2-[1-(6-methyl-pyridazin-3-yl)-piperidin-4-yl]-ethoxy}-benzo[d]isoxazole | 0.55 ± 0.14 | 0.20 ± 0.02 |
| Pirodavir | 20 ± 2 | 0.44 ± 0.34 |
| V-073 | 0.026 ± 0.023 | >300 |
| Pleconaril | >300 | >300 |

Data are expressed as $EC_{50}$ values [μM] and are means±for at least 3 independent experiments.

The results shown in Table 1 indicate that 3-ethoxy-6-{2-[1-(6-methyl-pyridazin-3-yl)-piperidin-4-yl]-ethoxy}-benzo[d]isoxazole is the most potent antiviral agent against EV71. Furthermore, 3-ethoxy-6-{2-[1-(6-methyl-pyridazin-3-yl)- piperidin-4-yl]-ethoxy}-benzo[d]isoxazole shows an approximate 36 fold decrease in $EC_{50}$ value for PV1 and an approximate 2 fold decrease in $EC_{50}$ value for EV71, in other words increased activity, when compared to Pirodavir. Comparatively, Pleconaril is inactive against both PV1 and EV71 ($EC_{50}$>300 μM).

Additionally, the results shown in Table 1 indicate that 3-ethoxy-6-{2-[1-(6-methyl-pyridazin-3-yl)-piperidin-4-yl]-ethoxy}-benzo[d]isoxazole was the only capsid binder with dual potency (submicromolar/nanomolar $EC_{50}$ values) against PV1 and EV71.

Thus the observed results for each of the four capsid binders against PV1 and EV71 are surprising, as it may have been thought that compounds with the same mode of action would display similar activity, or at least patterns of activity, across a range of viruses.

Whilst Table 1 shows the efficacy of 3-ethoxy-6-{2-[1-(6-methyl-pyridazin-3-yl)-piperidin-4-yl]-ethoxy}-benzo[d]isoxazole in reducing replication of PV1 and EV71, Table 2, discussed below, further shows that 3-ethoxy-6-{2-[1-(6-methyl-pyridazin-3-yl)-piperidin-4-yl]-ethoxy}-benzo[d]isoxazole is effective against a range of serotypes of the species HEV-A, HEV-B, HEV-C and HEV-D. PV1 is a poliovirus serotype classified as a member of the HEV-C species whereas EV71 is a non-polio enterovirus serotype classified as a member of the HEV-A species. Sequencing studies of the 5'-untranslated region indicate that the four human enterovirus species form two clusters, with viruses of HEV-C and HEV-D comprising cluster I and viruses of HEV-A and HEV-B comprising cluster II. Accordingly, the results in Table 1 demonstrate that 3-ethoxy-6-{2-[1-(6-methyl-pyridazin-3-yl)-piperidin-4-yl]-ethoxy}-benzo[d]isoxazole has activity against both cluster I and cluster II of the human enterovirus species.

Furthermore, the results provided in Table 2 further demonstrate the potent and broad enteroviral activity of 3-ethoxy-6-{2-[1-(6-methyl-pyridazin-3-yl)-piperidin-4-yl]-ethoxy}-benzo[d]isoxazole against a range of other serotypes from clusters I and II. The results were obtained by the methods described in Example 1.

TABLE 2

Enteroviral activity of 3-ethoxy-6-{2-[1-(6-methyl-pyridazin-3-yl)-piperidin-4-yl]-ethoxy}-benzo[d]isoxazole

| Enterovirus Serotype | Human Enterovirus species | 3-ethoxy-6-{2-[1-(6-methyl-pyridazin-3-yl)-piperidin-4-yl]-ethoxy}-benzo[d]isoxazole [$EC_{50}$ (μM)] |
|---|---|---|
| Echovirus 4 (E4) | HEV-B | 0.001 |
| Echovirus 9 (E9) | HEV-B | 0.003 |
| Echovirus 11 (E11) | HEV-B | 0.05 |
| Echovirus 30 (E30) | HEV-B | 1.6 |
| Coxsackievirus A9 (CVA9) | HEV-B | 0.40 |
| Coxsackievirus A16 (CVA16) | HEV-A | 1.1 |
| Coxsackievirus A21 (CVA21) | HEV-C | 0.3 |
| Poliovirus Type 2 (PV2) | HEV-C | 0.18 |
| Poliovirus Type 3 (PV3) | HEV-C | 0.018 |

The polio and non-polio enterovirus serotypes within the human enterovirus species HEV-A, HEV-B, HEV-C and HEV-D will be familiar to those skilled in the art and are described in such references as *Fields Virology* ibid.

In some embodiments the human enterovirus may be a poliovirus. Examples of poliovirus serotypes are PV1, PV2 and PV3 classified under the species Human enterovirus C (HEV-C). In some embodiments the poliovirus is poliovirus type 1 (PV1).

In some embodiments the human enterovirus may be a non-polio enterovirus, which is used herein to define serotypes selected from the coxsackieviruses A, coxsackieviruses B, echoviruses and the more recently classified enteroviruses.

Examples of coxsackievirus A and B serotypes are: CVA2, CVA3, CVA4, CVA5, CVA6, CVA7, CVA8, CVA10, CVA12, CVA14 and CVA16 classified under the species Human enterovirus A (HEV-A); serotypes CVB1, CVB2, CVB3, CVB4, CVB5, CVB6, CVA9 and CVA23 classified under the species Human enterovirus B (HEV-B); and serotypes CVA1, CVA11, CVA13, CVA17, CVA19, CVA20, CVA21, CVA22 and CVA24 classified under the species Human enterovirus C (HEV-C). In some embodiments the coxsackievirus is coxsackievirus type A9, A16 or A21

Examples of echovirus serotypes are: E1, E2, E3, E4, E5, E6, E7, E8, E9, E11, E12, E13, E14, E15, E16, E17, E18, E19, E20, E21, E24, E25, E26, E27, E29, E30, E31, E32 and E33 classified under the species Human enterovirus B (HEV-B). In some embodiments the echovirus is echovirus type E4, E9, E11 or E30.

Examples of the more recently classified enterovirus serotypes (EV68 onwards) are: EV71, EV76, EV89, EV90, EV91 and EV92 classified under the species Human enterovirus A (HEV-A); serotypes EV69, EV73, EV74, EV75, EV77, EV78, EV79, EV80, EV81, EV82, EV83, EV84, EV85, EV86, EV87, EV88, EV93, EV97, EV98, EV100, EV101, EV106 and EV107 classified under the species Human enterovirus B (HEV-B); serotypes EV95, EV96, EV99, EV102, EV104, EV105 and EV109 classified under the species Human enterovirus C (HEV-C); and serotypes EV68, EV70 and EV94 classified under the species Human enterovirus D (HEV-D). In some embodiments the non-polio enterovirus is one of the more recently classified enteroviruses, such as enterovirus type 71 (EV71).

Diagnosis of an enteroviral infection caused by a serotype of one or more of the species Human enterovirus A, Human enterovirus B, Human enterovirus C and Human enterovirus D in a subject may be performed in a number of different ways. Samples may be tested using laboratory diagnostic methods including serological tests, viral isolation by cell culture and polymerase chain reaction (PCR). Virus may be detected in samples taken from the body, such as the throat or in fecal samples or samples of the affected site such as cerebrospinal fluid (CSF), biopsy material and skin lesions. In some embodiments, evidence of a recent infection may be indicated by a four-fold rise in the level of neutralizing antibody in the acute phase specimens as against the convalescent phase specimens.

In some embodiments, laboratory diagnosis is not possible, or at least less preferable. For example, laboratory diagnosis may be too time consuming in view of the risk of or onset of an infection which may require immediate diagnosis for preventative or therapeutic treatment. Clinical diagnosis of the symptoms associated with diseases and conditions caused by enteroviral infections may therefore be relied upon to diagnose at risk populations as well as individuals suffering from an infection for the purpose of preventative or therapeutic treatment. Such clinical diagnosis may involve a comparison of symptoms and/or epidemiological factors between the subject and other portions of the population. In view of the broad spectrum enteroviral activity of 3-ethoxy-6-{2-[1-(6-methyl-pyridazin-3-yl)-piperidin-4-yl]-ethoxy}-benzo[d]isoxazole it may not be necessary to identify the particular serotype or serotypes responsible for a particular condition before prescribing treatment. This can be advantageous in the circumstances described above.

Accordingly, in some embodiments the methods of the invention comprise a diagnosis step, whereby a subject is selected on the basis of requiring treatment, alleviation, prevention or reduction of symptoms, diseases or conditions associated with an enteroviral infection caused by a serotype of one or more of the species Human enterovirus A, Human enterovirus B, Human enterovirus C and Human enterovirus D. In some embodiments the medicament of the invention is intended for use by a subject selected on the basis of requiring treatment, alleviation, prevention or reduction of symptoms, diseases or conditions associated with an enteroviral infection caused by a serotype of one or more of the species Human enterovirus A, Human enterovirus B, Human enterovirus C and Human enterovirus D.

The symptoms, diseases or conditions that result from or are associated with infection caused by a poliovirus (such as PV1) include poliomyelitis i.e. polio, paralysis, aseptic meningitis and undifferentiated/non-specific febrile illness.

The symptoms, diseases or conditions that result from or are associated with infection caused by a non-polio enterovirus generally include but are not limited to dermatologic manifestations such as hand foot and mouth disease (skin lesions), exanthema (rashes) and blisters; throat manifestations such as herpingina (vesicular eruption and inflammation of the throat), mouth ulcers and acute lymphatic or nodular pharyngitis; viral respiratory conditions such as acute/upper respiratory illness, pneumonia, bronchiolitis, pneumonitis of infants, croup and the common cold; neurological manifestations such as CNS involvement including neurogenic i.e. non-cardiogenic pulmonary oedema and cardiopulmonary failure after CNS involvement, aseptic meningitis (inflammation of the brain lining) including nuchal rigidity, encephalitis (inflammation of the brain) including brainstem encephalitis, meningoencephalitis which causes significant morbidity especially in infants and young children, paralysis, acute flaccid paralysis, polio-like paresis, epidemic myalgia (muscle pain) and muscle weakness, ataxia, Guillain-Barré syndrome, mylclonus, tremor and impaired consciousness; heart manifestations such as myocarditis (inflammation of the heart muscle) and pericarditis (inflammation of the lining outside the heart); gastrointestinal manifestations including infantile diarrhoea and gastroenteritis; and other clinical manifestations including pancreatitis, fever, chills, pleurodynia, sepsis, severe systemic infection in infants, hepatic disturbances, undifferentiated/non-specific febrile illness, postviral fatigue syndrome, acute hemorrhagic conjunctivitis, headache, nausea and vomiting.

Particular diseases or conditions generally associated with coxsackievirus A serotype infections include herpingina, acute lymphatic or nodular pharyngitis, aseptic meningitis, paralysis, exanthema, hand foot and mouth disease, pneumonitis of infants, the common cold, hepatitis, infantile diarrhoea, acute hemorrhagic conjunctivitis. Diseases or conditions generally associated with coxsackievirus B serotype infections include pleurodynia, aseptic meningitis, paralysis, severe systemic infection in infants, meningoencephalitis and mycarditis, pericarditis, myocarditis, upper respiratory illness and pneumonia, rash, hepatitis, undifferentiated or nonspecific febrile illness and postviral fatigue syndrome.

Particular diseases or conditions generally associated with echoviruses include aspectic meningitis, paralysis, encephalitis, ataxia or Guillain-Barré syndrome, exanthema, respiratory diseases, diarrhea, epidemic myalgia, pericarditis, myocarditis and hepatic disturbances.

Particular diseases or conditions generally associated with more recently classified enteroviruses (such as EV68 onwards) include pneumonia, bronchiolitis, acute hemorrhagic conjunctivitis, paralysis, meningoencephalitis, meningitis, encephalitis and hand foot and mouth disease. More particular symptoms, diseases or conditions resulting from or associated with an EV71 infection include dermatologic manifestations such as rashes, blisters, herpangina, hand foot and mouth disease and neurological manifestations such as brain-stem encephalitis, neurogenic pulmonary edema/hemorrhage and cardiopulmonary failure after CNS involvement, aseptic meningitis, polio-like paresis, acute flaccid paralysis, ataxia, mylclonus, intention, tremor and impaired consciousness as well as acute respiratory diseases such as pharyngitis, croup, bronchiolitis and pneumonia. The long-term neurological and psychiatric effects of EV71 infection are also not well understood though there is evidence to suggest that CNS involvement associated with an EV71 infection may be implicated in the development of attention-deficit/hyperactivity disorder-related symptoms.

In some embodiments, it may be possible to prevent or reduce the risk of drug resistance development during monotherapy by using a combination of antiviral agents. Combination therapy is particularly important when there is a high risk of viral mutations leading to resistance. Such agents should ideally have an unrelated mode of action as this may reduce the chance of developing resistance to treatment. Ideally, both agents should be combined to result in potent activity and a reduced risk of resistance development.

Accordingly, the use of 3-ethoxy-6-{2-[1-(6-methyl-pyridazin-3-yl)-piperidin-4-yl]-ethoxy}-benzo[d]isoxazole or a pharmaceutically acceptable salt thereof in combination with a second anti-enteroviral agent to treat, alleviate, prevent or reduce the incidence of symptoms, diseases or conditions associated with an enteroviral infection caused by a serotype of one or more of the species Human enterovirus A, Human enterovirus B, Human enterovirus C and Human enterovirus D provides another aspect of the invention. The second anti-enteroviral agent may include but is not limited to compounds such as ribavirin, Pirodavir, Pleconaril, V-073, Rupintrivir (AG-7088), 2'-C-Met-Cyt, Enviroxime, TTP-8307 and MDL-860. It will also be understood that the second anti-enteroviral agent may be interferon or a vaccine such as a polio vaccine (OPV-Sabin or IPV-Salk).

TABLE 3

Selected anti-enteroviral compounds and their structure.

| Compound Name | Structure |
|---|---|
| Pirodavir | 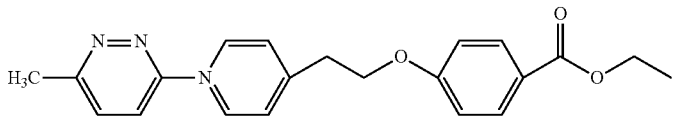 |

TABLE 3-continued
Selected anti-enteroviral compounds and their structure.
| Compound Name | Structure |
|---|---|
| V-073 | 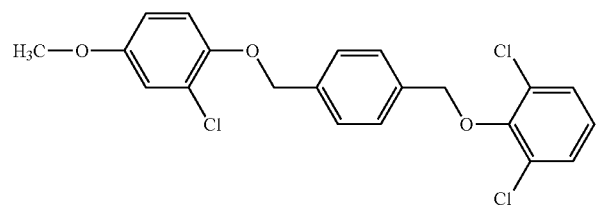 [SMILES: COc1ccc(OCc2ccc(COc3c(Cl)cccc3Cl)cc2)c(Cl)c1] |
| Pleconaril | 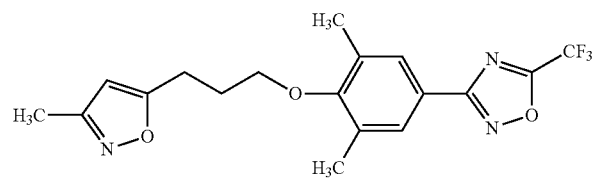 |
| Rupintrivir (AG-7088) | 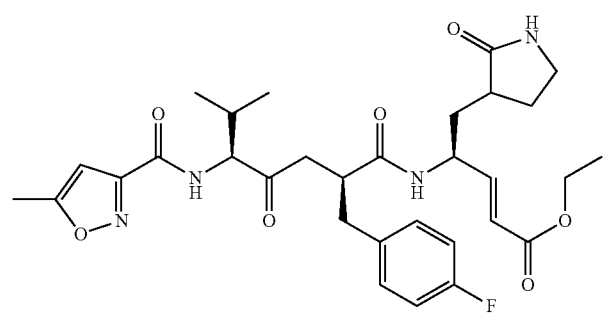 [SMILES: CCOC(=O)/C=C/[C@H](CC1CCNC1=O)NC(=O)[C@H](CC(=O)[C@@H](NC(=O)c1cc(C)on1)C(C)C)Cc1ccc(F)cc1] |
| 2'-C-Met-Cyt | 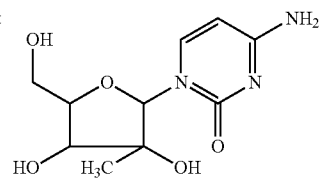 |
| Enviroxime | 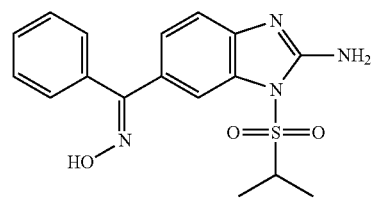 [SMILES: CC(C)S(=O)(=O)n1c(N)nc2ccc(/C(=N/O)c3ccccc3)cc21] |
| TTP-8307 | 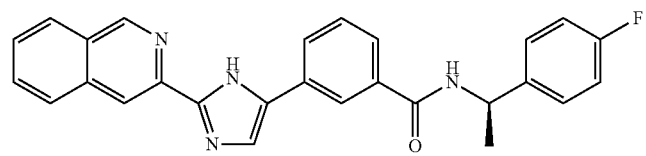 [SMILES: C[C@@H](NC(=O)c1cccc(-c2cnc(-c3cc4ccccc4cn3)[nH]2)c1)c1ccc(F)cc1] |
| MDL-860 | 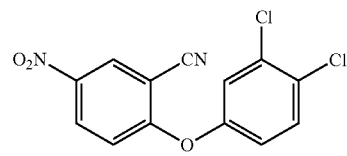 [SMILES: N#Cc1cc([N+](=O)[O-])ccc1Oc1ccc(Cl)c(Cl)c1] |

TABLE 3-continued

Selected anti-enteroviral compounds and their structure.

| Compound Name | Structure |
| --- | --- |
| Ribavirin | (structure shown) |

Figure 2:
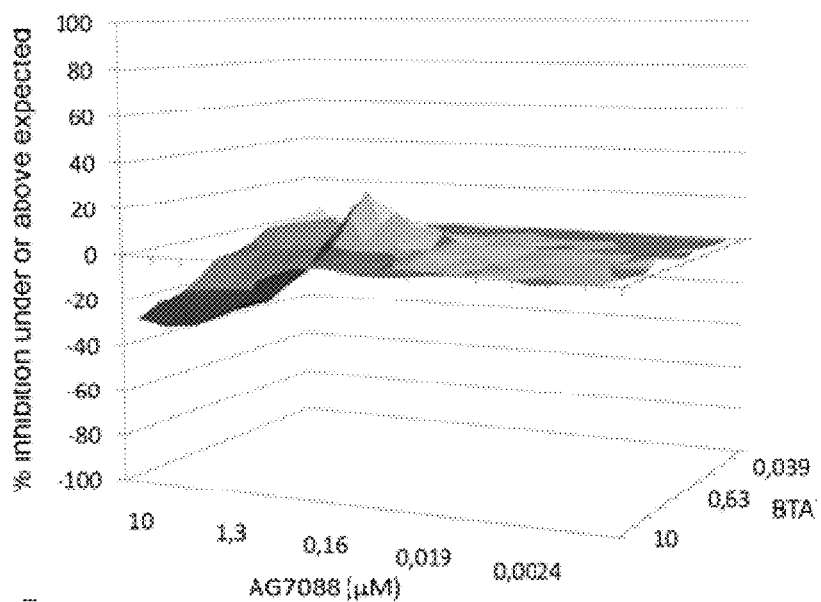
FIG. 2: Shows the combined antiviral activity of 3-ethoxy-6-{2-[1-(6-methyl-pyridazin-3-yl)-piperidin-4-yl]-ethoxy}-benzo[d]isoxazole (BTA; concentration in µM) with Rupintrivir i.e. AG-7088 (Representation C) and enviroxime (Representation D) respectively as against enterovirus 71 BrCr strain (EV71).
Figure 2:
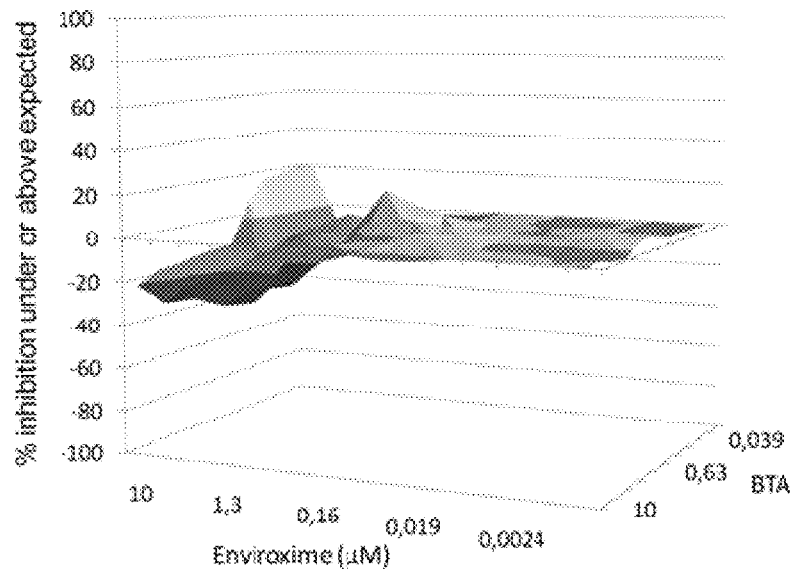

In some embodiments, the dosage amounts of 3-ethoxy-6-{2-[1-(6-methyl-pyridazin-3-yl)-piperidin-4-yl]-ethoxy}-benzo[d]isoxazole or a pharmaceutically acceptable salt thereof and the second anti-enteroviral agent in the combinations are such that they may provide an additive or synergistic effect. In FIGS. 1 and 2, and as described in Example 2, a positive value for "% inhibition under or above expected" indicates synergy. As can be seen in FIG. 1, combinations of 3-ethoxy-6-{2-[1-(6-methyl-pyridazin-3-yl)-piperidin-4-yl]-ethoxy}-benzo[d]isoxazole together with AG7088 or Enviroxime provides slight synergy against poliovirus Sabin 1 (PV-1) at certain concentrations. As can be seen in FIG. 2, combinations of 3-ethoxy-6-{2-[1-(6-methyl-pyridazin-3-yl)-piperidin-4-yl]-ethoxy}-benzo[d]isoxazole together with AG7088 or Enviroxime provides slight synergy against enterovirus 71 BrCr strain (EV-71) at certain concentrations. It will be understood that 3-ethoxy-6-{2-[1-(6-methyl-pyridazin-3-yl)-piperidin-4-yl]-ethoxy}-benzo[d]isoxazole, AG7088 and enviroxime each have different modes of action.

The use of 3-ethoxy-6-{2-[1-(6-methyl-pyridazin-3-yl)-piperidin-4-yl]-ethoxy}-benzo[d]isoxazole or a pharmaceutically acceptable salt thereof in combination with the second anti-enteroviral agent may be by separate, simultaneous or sequential administration.

In some embodiments 3-ethoxy-6-{2-[1-(6-methyl-pyridazin-3-yl)-piperidin-4-yl]-ethoxy}-benzo[d]isoxazole or a pharmaceutically acceptable salt thereof and the second anti-enteroviral agent are provided in admixture as a composition. Typically such an admixture also comprises a pharmaceutically-acceptable adjuvant, diluent or carrier.

In other embodiments 3-ethoxy-6-{2-[1-(6-methyl-pyridazin-3-yl)-piperidin-4-yl]-ethoxy}-benzo[d]isoxazole or pharmaceutically acceptable salt thereof and the second anti-enteroviral agent are provided as a kit of parts. In these embodiments each component of the kit of parts is provided in a form that is suitable for administration in conjunction with the other component. In this respect the two components in the kit of parts may be: (i) provided as separate formulations (i.e. independently of one another), which are subsequently brought together for use in conjunction with each other in combination therapy; or (ii) packaged and presented together as separate components of a combination pack for use in conjunction with each other in combination therapy. Typically each component of such a kit of parts also comprises a pharmaceutically-acceptable adjuvant, diluent or carrier.

According to the invention, 3-ethoxy-6-{2-[1-(6-methyl-pyridazin-3-yl)-piperidin-4-yl]-ethoxy}-benzo[d]isoxazole or a pharmaceutically acceptable salt thereof (or a combination comprising a second anti-enteroviral agent) may be administered by any means including orally, nasally, intravenously or by inhalation or insufflation. In some embodiments 3-ethoxy-6-{2-[1-(6-methyl-pyridazin-3-yl)-piperidin-4-yl]-ethoxy}-benzo[d]isoxazole or a pharmaceutically acceptable salt thereof (or a combination comprising a second anti-enteroviral agent) is formulated for nasal administration, intravenous administration, inhalation or insufflation. Oral administration is preferred and accordingly, in some embodiments, 3-ethoxy-6-{2-[1-(6-methyl-pyridazin-3-yl)-piperidin-4-yl]-ethoxy}-benzo[d]isoxazole or a pharmaceutically acceptable salt thereof (or a combination comprising a second anti-enteroviral agent) is formulated for oral delivery.

Pharmaceutical formulations include those suitable for oral (including oral enteral administration), rectal, nasal, topical (including buccal and sub-lingual), vaginal or parenteral (including intramuscular, sub-cutaneous and intravenous administration) or in a form suitable for administration by inhalation or insufflation. Preferably the formulations are provided in a form suitable for oral or nasal administration or by inhalation or insufflation or intravenous injection. Liquids are preferred for intravenous administration. In some embodiments the formulation is suitable for administration by intranasal delivery, inhalation or insufflation. Liquids and powders are generally preferred for intranasal administration. In some embodiments the formulation is suitable for oral administration. Oral formulations are particularly preferred and may be in a liquid or a solid form.

Carriers and/or diluents include any and all solvents (including where used to form a solvate such as a hydrate), dispersion media, coatings, antibacterial and antifungal agents, isotonic and absorption delaying agents and the like. The use of such media and agents for pharmaceutical active substances is well known in the art. Carriers and excipients are ideally "pharmaceutically acceptable" meaning that the carrier or excipient is substantially compatible with the other ingredients of the composition or formulation and is substantially not deleterious to a subject. The active ingredient may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: *The Science and Practice of Pharmacy*, 21st Ed., 2005, Lippincott Williams & Wilkins). Examples of suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Suitable liquid form preparations include solutions, suspensions, emulsions and syrups, for example, water or water-propylene glycol solutions. Aqueous solutions suitable for oral use can be prepared by dissolving 3-ethoxy-6-{2-[1-(6-methyl-pyridazin-3-yl)-piperidin-4-yl]-ethoxy}-benzo[d]

isoxazole or a pharmaceutically acceptable salt thereof in water and adding suitable colorants, flavours, stabilizing and thickening agents as desired. Aqueous suspensions suitable for oral use can be made by dispersing the finely divided active component in water with a viscous material, such as natural or synthetic gums, resins, methylcellulose, sodium carboxymethylcellulose or other well known suspending agents.

Solid form preparations include powders, tablets, pills, capsules, cachets, lozenges, suppositories, and dispensable granules. Suitable solid form preparations may also include those which are intended to be converted, shortly before use, to liquid form preparations for oral administration. The term "preparation" is intended to include the formulation of 3-ethoxy-6-{2-[1-(6-methyl-pyridazin-3-yl)-piperidin-4-yl]-ethoxy}-benzo[d]isoxazole or a pharmaceutically acceptable salt thereof with encapsulating material as carrier, thereby providing a capsule in which the active component, with or without carriers, is surrounded by a carrier. In the form of a dry powder the preparation may be, for example, a mix of the compound in a suitable powder base such as glucose, lactose, starch, starch derivatives such as hydroxypropylmethyl cellulose and polyvinylpyrrolidone (PVP). Lactose is a preferred powder base. The powdered compound or composition may be presented in a unit dose form. In powders, the carrier is a finely divided solid that is in a mixture with the finely divided active component. In tablets, the active component is mixed with the carrier having the necessary binding capacity in suitable proportions and compacted in the shape and size desired. Preferred solid form preparations for oral administration are tablets, pills, lozenges and capsules, with tablets and capsules being particularly preferred.

In formulations intended for administration to the respiratory tract, including intranasal formulations, the compound will generally have a small particle size. Such a particle size may be obtained by means known in the art such as spray drying or micronisation. Administration to the respiratory tract may be achieved by applying solutions or suspensions directly to the nasal cavity by conventional means, for example with a dropper, pipette or spray. The formulations may be provided in single or multidose form. This may be achieved for example by an aerosol formulation in which the active ingredient is provided by means of a pressurised metered dose inhaler or in a pressurised pack with a suitable propellant such as hydrofluoroalkane (HFA) propellant. Dry powder inhalers and nebulizers that do not use propellants may also be used.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi. Pharmaceutical forms suitable for injectable use may be delivered by any appropriate route including intravenous, intramuscular, intracerebral, intrathecal, epidural injection or infusion.

When desired, formulations adapted to give sustained release of the active ingredient may be employed.

In a unit dose form, the preparation is subdivided into unit doses containing appropriate quantities of 3-ethoxy-6-{2-[1-(6-methyl-pyridazin-3-yl)-piperidin-4-yl]-ethoxy}-benzo[d]isoxazole or a pharmaceutically acceptable salt thereof and in such form may be employed as solids, such as tablets or filled capsules, or liquids such as solutions, suspensions, emulsions, elixirs, or capsules filled with the same, all for oral use, in the form of suppositories for rectal administration or in the form of sterile injectable solutions for parenteral (including subcutaneous) use. The unit dosage form can be a packaged preparation, the package containing discrete quantities of preparation such as tablets, capsules and powders in vials or ampoules. The unit dosage form can also be a capsule, table, cachet, or lozenge itself or it can be the appropriate number of any of these in packaged form. Such unit dosage forms may contain any suitable effective amount of the active ingredient commensurate with the intended daily dosage range to be employed. Formulations containing 0.1 to 1000 milligrams of active ingredient per dosage form provide representative unit dosage forms. In some embodiments the 3-ethoxy-6-{2-[1-(6-methyl-pyridazin-3-yl)-piperidin-4-yl]-ethoxy}-benzo[d]isoxazole or a pharmaceutically acceptable salt thereof is administered in a dosage amount of from 1 mg to 800 mg per day, from 1 mg to 600 mg per day, from 1 mg to 400 mg per day, 1 mg to 200 mg per day or from 1 mg to 100 mg per day. The dosage forms may comprise, as the active component, either a compound of the invention or a pharmaceutically acceptable salt of a compound of the invention. The amount of active compound in therapeutically useful compositions should be sufficient that a suitable dosage will be obtained. Suitable dosage amounts and dosing regimens can be determined by the attending physician and may depend on the particular condition being treated, the severity of the condition as well as the general age, health and weight of the subject.

3-ethoxy-6-{2-[1-(6-methyl-pyridazin-3-yl)-piperidin-4-yl]-ethoxy}-benzo[d]isoxazole or a pharmaceutically acceptable salt thereof is administered in an amount which, when administered according to the desired dosing regimen, attains, or at least partially attains, the desired effect of treatment, alleviation, prevention or reduction of symptoms, diseases or conditions associated with an enteroviral infection caused by a serotype of one or more of the species Human enterovirus A, Human enterovirus B, Human enterovirus C and Human enterovirus D. As used herein, treatment and alleviation of symptoms, diseases or conditions may include alleviating or ameliorating the symptoms, diseases or conditions associated with an enteroviral infection being treated, including reducing the severity and/or frequency of the enteroviral infection. As used herein, prevention or reduction of symptoms, diseases or conditions may include preventing or delaying the onset of, inhibiting the progression of, or halting or reversing altogether the onset or progression of the particular symptoms, disease or condition associated with an enteroviral infection.

Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety.

In some embodiments it may be preferable to formulate the 3-ethoxy-6-{2-[1-(6-methyl-pyridazin-3-yl)-piperidin-4-yl]-ethoxy}-benzo[d]isoxazole as a pharmaceutically acceptable salt such as its bis-dihydrogenphosphate and/or sulfate salt as disclosed in WO2009/143571 (the entire contents of which is incorporated herein by reference).

In some embodiments the medicaments of the invention comprising 3-ethoxy-6-{2-[1-(6-methyl-pyridazin-3-yl)-piperidin-4-yl]-ethoxy}-benzo[d]isoxazole or a pharmaceutically acceptable salt thereof may be provided with instructions for use of the medicament. In some embodiments the methods of the invention, and the use of 3-ethoxy-6-{2-[1-(6-methyl-pyridazin-3-yl)-piperidin-4-yl]-ethoxy}-benzo[d] isoxazole or a pharmaceutically acceptable salt thereof in the stated applications, may further comprise the use of instructions.

In these embodiments the instructions may indicate a particular dosing regime, mode of administration, or otherwise, so as to indicate to the patient or physician, for example, how the medicament or method is to be applied to the intended application. For example the instructions may indicate how to use a medicament, or perform a method, in the treatment or alleviation of symptoms, diseases or conditions associated with an enteroviral infection caused by a serotype of one or more of the species Human enterovirus A, Human enterovirus B, Human enterovirus C and Human enterovirus D. The instructions may indicate how to use a medicament, or perform a method, in the reduction of the incidence of enteroviral infection caused by a serotype of one or more of the species Human enterovirus A, Human enterovirus B, Human enterovirus C and Human enterovirus D. Such instructions may indicate the separate, simultaneous or sequential administration of 3-ethoxy-6-{2-[1-(6-methyl-pyridazin-3-yl)-piperidin-4-yl]-ethoxy}-benzo[d]isoxazole or a pharmaceutically acceptable salt thereof and another medicament, such as a second anti-enteroviral agent.

As used herein, the term "subject" refers to any subject, preferably a vertebrate subject, and even more preferably a mammalian subject, for whom treatment, alleviation, prevention or reduction of symptoms, diseases or conditions associated with enteroviruses is desired. Typically the subject is a human.

Those skilled in the art will appreciate that the invention described herein is susceptible to variations and modifications other than those specifically described.

EXAMPLES

The invention will now be described without limitation by reference to the examples which follow.

Example 1 a) In Vitro Assay to Determine Antiviral Activity Against Coxsackievirus A9, A16, A21, Echovirus 11, Poliovirus 1, Poliovirus 2, Poliovirus 3 and *Enterovirus* 71

The antiviral activity of the selected compounds was determined using a colorimetric cytopathic effect (CPE) reduction assay and data are expressed as $EC_{50}$, being the concentration of compound that inhibits virus-induced CPE formation by 50%. Cells, grown to confluency in 96-well plates were infected with 100 $CCID_{50}$ (50% cell culture infective dose) and treated with serial dilutions of the compound. The cultures were incubated at 37° C. for 3 days, until complete CPE was observed in the infected and untreated virus control (VC). Following incubation with MTS/PMS the optical density of each well was read at 498 nm in a microplate reader. CPE values were calculated as follows: % CPE=[$OD_{CC}$−$OD_{Virus+Compound}$]/[$OD_{CC}$−$OD_{VC}$]. In these formulae, $OD_{CC}$ corresponds to the optical density of the uninfected and untreated cell cultures, $OD_{VC}$ represents the infected and untreated cell cultures and $OD_{Virus+Compound}$ are virus-infected cell cultures, treated with a given concentration of compound.

b) In Vitro Assay to Determine Antiviral Activity Against Echovirus 4, 9 and 30

The antiviral activity of the selected compounds was determined using a colorimetric cytopathic effect (CPE) reduction assay and data are expressed as $EC_{50}$, being the concentration of compound that inhibits virus-induced CPE formation by 50%. Compounds were serially diluted in 96-well plates and cells infected with virus added to plates. Virus was added at a multiplicity of infection which produces 100% CPE in infected and untreated virus control wells (VC). The cultures were incubated at 37° C. for 4 days. Following incubation, cell viability was assessed by MTT with the optical density of each well was read at 540 nm in a microplate reader. CPE values were calculated as follows: % CPE=[$OD_{CC}$−$OD_{Virus+Compound}$]/[$OD_{CC}$−$OD_{VC}$]. In these formulae, $OD_{CC}$ corresponds to the optical density of the uninfected and untreated cell cultures, $OD_{VC}$ represents the infected and untreated cell cultures and $OD_{Virus+Compound}$ are virus-infected cell cultures, treated with a given concentration of compound. $EC_{50}$ values were calculated from the percent cell protection results by non-linear regression analysis.

Example 2

Combination Assay to Determine Combined Activity of Anti-Enteroviral Compounds Against Poliovirus 1 (PV1) and *Enterovirus* 71 (EV71)

The effect of drug-drug combinations of 3-ethoxy-6-{2-[1-(6-methyl-pyridazin-3-yl)-piperidin-4-yl]-ethoxy}-benzo[d] isoxazole were evaluated using the method described by Prichard and Shipman, analyzing data for synergism, antagonism, or additive effects (Prichard, M. N., and Shipman, C., Jr., "A three-dimensional model to analyse drug-drug interactions" *Antiviral Res.* (1990) 14: 181-205). When a combination is additive, data points form a horizontal surface that equals the zero plane. A surface that lies above the zero plane indicates a synergistic effect of the combination, a surface below the zero plane indicates antagonism.

3-Ethoxy-6-{2-[1-(6-methyl-pyridazin-3-yl)-piperidin-4-yl]-ethoxy}-benzo[d]isoxazole (a capsid binder), Rupintrivir i.e. AG-7088 (a protease inhibitor) and Enviroxime (a 3A-targeting compound) were selected as anti-enteroviral compounds with unrelated modes of action for testing in combination against PV1 and EV71. Note that the PV1 and EV71 values for Rupintrivir i.e. AG-7088 alone were determined to be $EC_{50}$ 4.5±0.36 µM and 0.90±0.07 µM respectively and the PV1 and EV71 values for Enviroxime alone were determined to be 0.79±0.13 µM and 0.45±0.12 µM respectively.

The results of the combination studies are presented in FIGS. 1 and 2. Values under the zero plane indicate antagonistic activity, values in the zero plane indicate additive activity, and values above the zero plane indicate synergistic activity. All data points are averages of four independent experiments. All combinations provided an additive to slightly synergistic antiviral effect at certain concentrations, for both viruses studied. There is no known evidence to suggest that these molecules may interfere with each others mechanism of action. For each possible combination of 3-ethoxy-6-{2-[1-(6-methyl-pyridazin-3-yl)-piperidin-4-yl]-ethoxy}-benzo[d]isoxazole, data points resulted in a more or less horizontal surface that equals the zero plane although some trend to slight synergistic activity was noted.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is know, is not, and should not be taken as an acknowledgement or admission or any form of suggestion that that prior publication, or information derived from it, or known matter forms part of the common general knowledge in the field of endeavour to which this specification relates.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for treating, alleviating, or reducing an enteroviral infection caused by a serotype of poliovirus 1 (PV1) or enterovirus 71 (EV71) comprising administering 3-ethoxy-6-{2-[1-(6-methyl-pyridazin-3-yl)-piperidin-4-yl]-ethoxy}-benzo[d]isoxazole or a pharmaceutically acceptable salt thereof to a subject suffering from said infection, and further comprising administering a second anti-enteroviral agent, wherein the second anti-enteroviral agent is rupintrivir or enviroxime.

2. The method according to claim 1 further comprising the step of selecting a subject on the basis of requiring treatment, alleviation, or reduction of symptoms, diseases or conditions associated with an enteroviral infection caused by a serotype of poliovirus 1 (PV1) or enterovirus 71 (EV71).

3. The method according to claim 1 wherein the serotype is poliovirus 1 (PV1).

4. The method according to claim 1 wherein the serotype is enterovirus 71 (EV71).

5. The method according to claim 1 wherein the second anti-enteroviral agent is rupintrivir.

6. The method according to claim 1 wherein the second anti-enteroviral agent is enviroxime.

7. The method according to claim 1 wherein administering the second anti-enteroviral agent is by separate, simultaneous or sequential administration.

* * * * *